United States Patent [19]

Rosenthal et al.

[11] 4,402,691
[45] Sep. 6, 1983

[54] ASEPTIC CONNECTION BARRIER SYSTEM AND METHOD

[75] Inventors: Arthur L. Rosenthal, Guilford; Bruce H. Wilson, Madison, both of Conn.

[73] Assignee: The Clinipad Corporation, Guilford, Conn.

[21] Appl. No.: 286,474

[22] Filed: Jul. 24, 1981

[51] Int. Cl.³ ............................................. A61M 3/00
[52] U.S. Cl. .................................... 604/411; 604/29; 604/905
[58] Field of Search ............... 128/247, 214 R, 214 G, 128/214 F, 215, 214.2, 334 C, 213 A, 133; 251/149.1, 149.9; 285/DIG. 2, 260, 38, 27, 45, 423, 21; 215/249, 251, 274, 247

[56] References Cited

U.S. PATENT DOCUMENTS

| | | | |
|---|---|---|---|
| 3,456,965 | 7/1969 | Gajewski et al. | 128/334 C |
| 3,538,915 | 11/1970 | Frampton et al. | 128/214 R |
| 4,006,744 | 2/1977 | Steer | 128/214 R |
| 4,043,333 | 8/1977 | Munsch | 128/214 G |
| 4,059,105 | 11/1977 | Cutruzzula et al. | 128/214 R X |
| 4,122,857 | 10/1978 | Haerr | 128/133 X |
| 4,176,756 | 12/1979 | Gellman | 215/274 |
| 4,200,107 | 4/1980 | Reid | 128/334 C |
| 4,340,052 | 7/1982 | Dennehey et al. | 128/247 |

OTHER PUBLICATIONS

"Zimmer Product Encyclopedia", Jun. 1978, p. B194.

Primary Examiner—Richard J. Apley
Assistant Examiner—Michelle N. Lester
Attorney, Agent, or Firm—St. Onge, Steward, Johnston & Reens

[57] ABSTRACT

An aseptic protective barrier device around sterile medical solution administration conduit connections is provided by an aseptic connection barrier system and method which reduces patient inconvenience, mess and chance of leakage and minimizes the risk of touch contamination during application while ensuring continuous antiseptic activity around the entire connection site. A barrier device is comprised of a contoured plastic housing formed by mating cavity halves joined along a hinge line, an absorbent member contained within the interior of the housing and a sealing tab attached to one of the housing halves for holding them together when folded along the hinge line. In use, the absorbent member has antiseptic solution applied to it and the housing is positioned to surround the connection site and compress the absorbent member and sealed in place to form a surrounding protective barrier and seal. The plastic protection enclosure barrier device is advantageously removably held on an applicator support, such as a card, in the open position to facilitate wetting of the inner absorbent member and provide a convenient and easy means for handling to facilitate application to the connection site.

5 Claims, 10 Drawing Figures

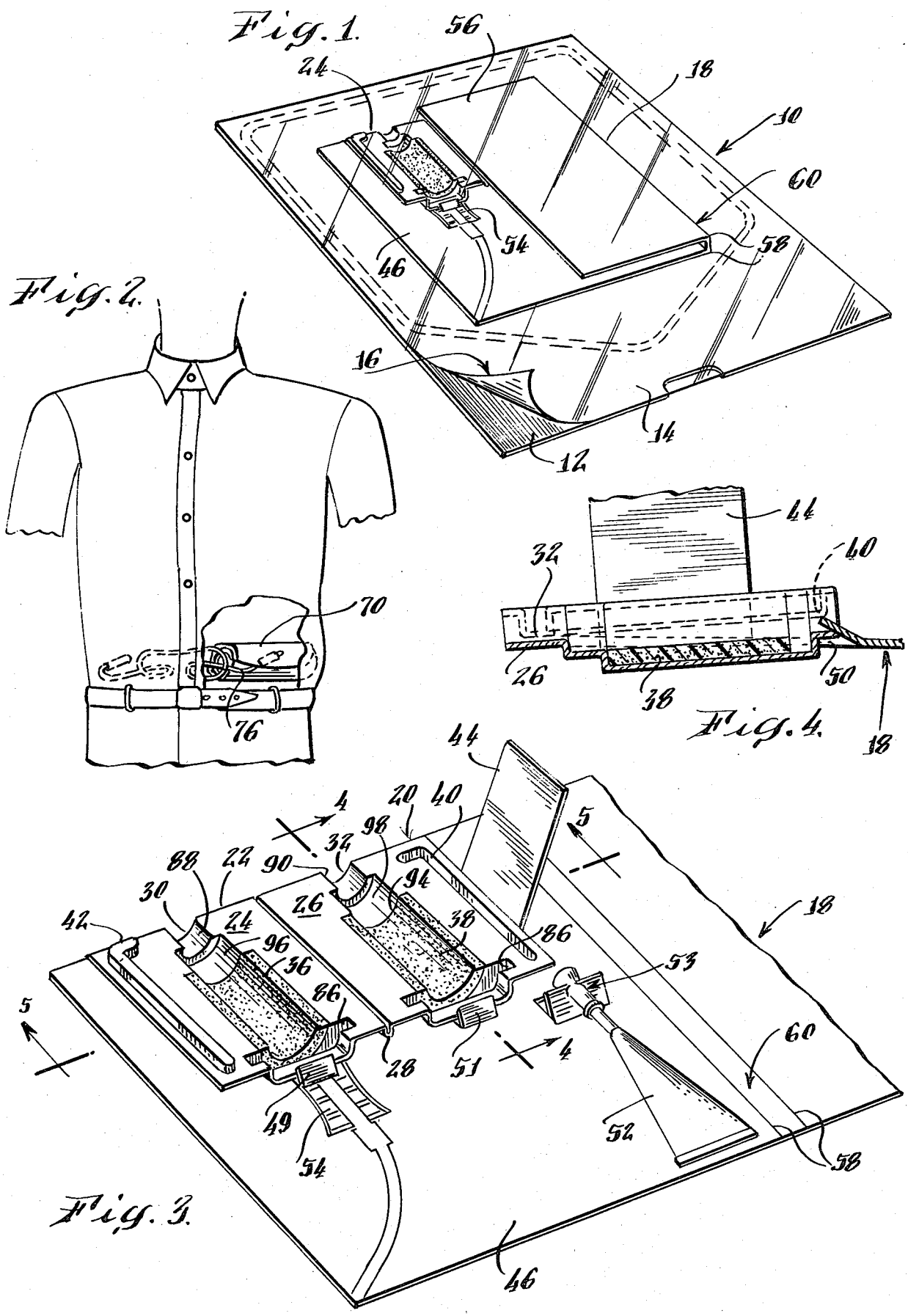

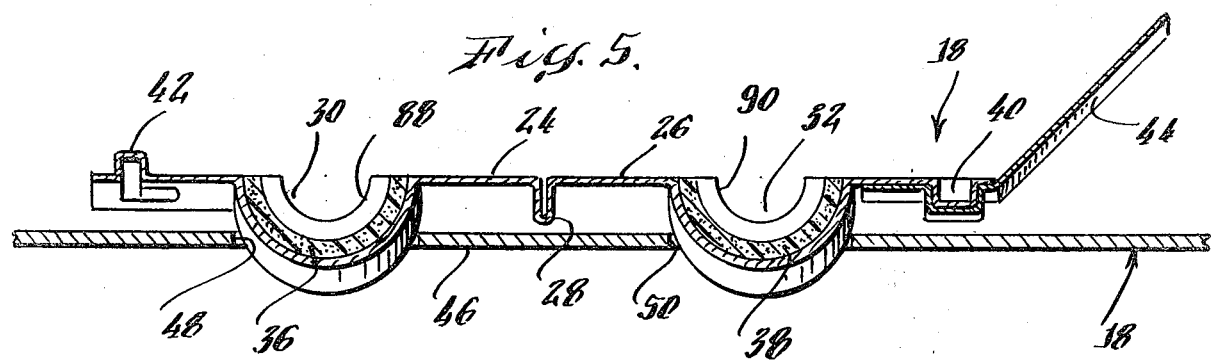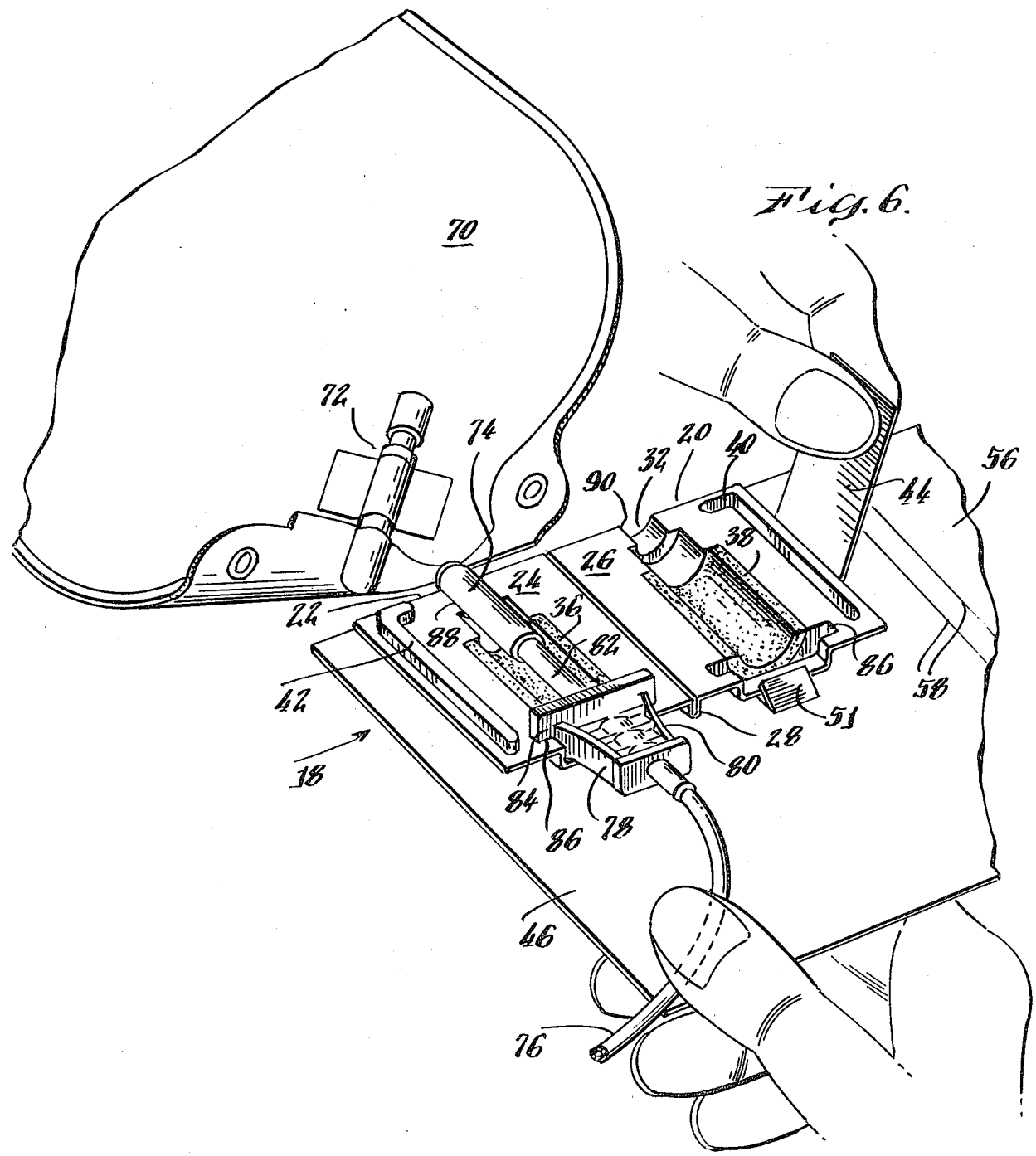

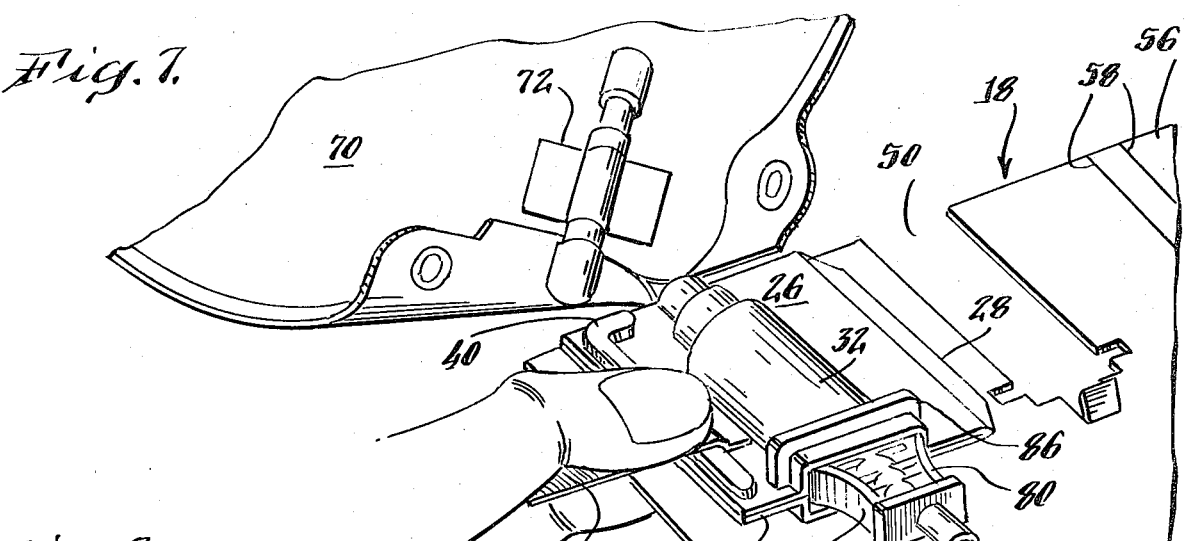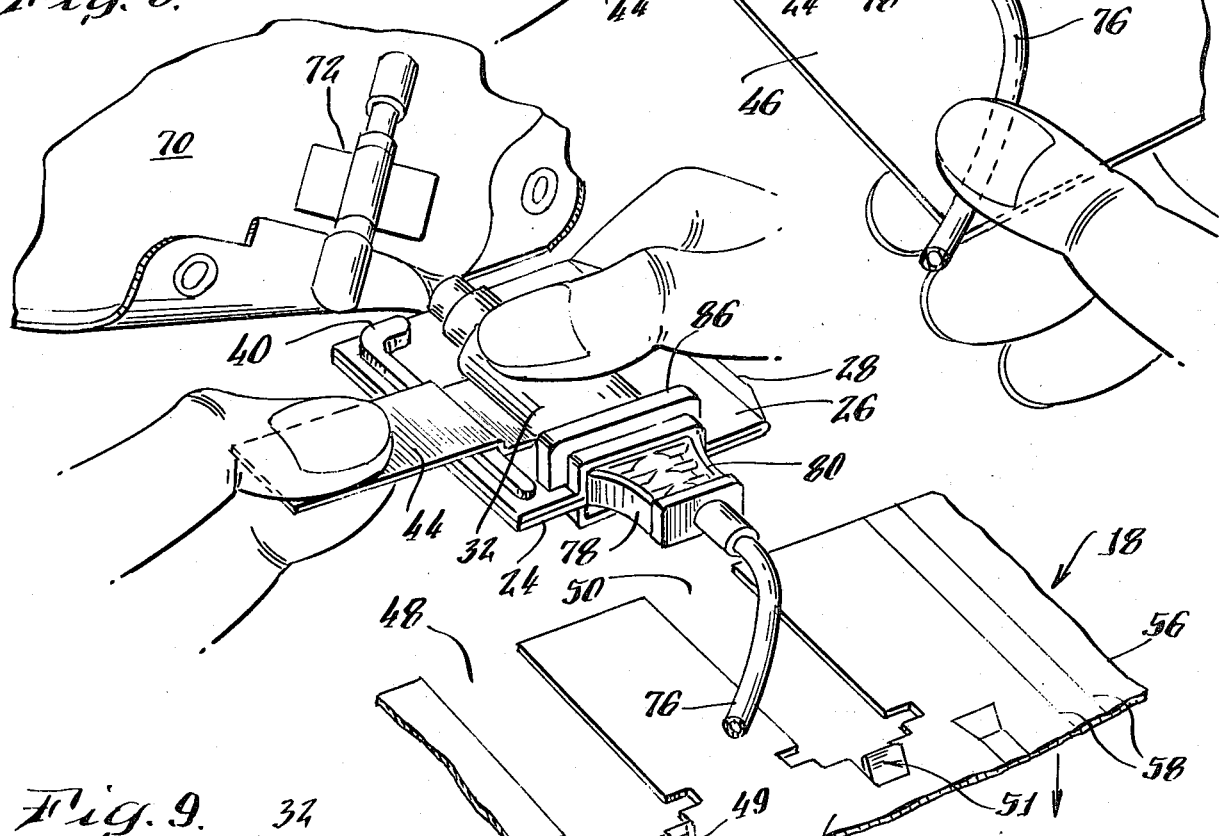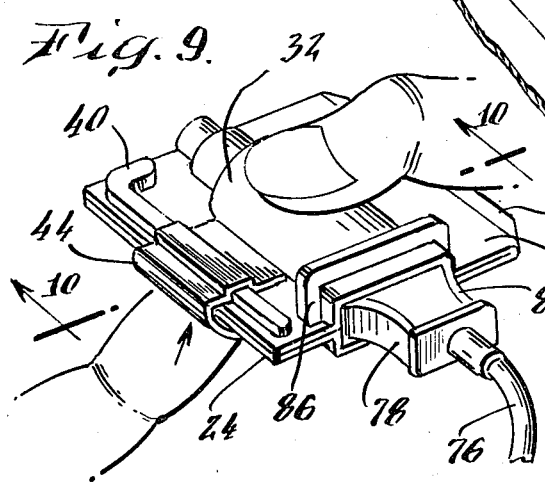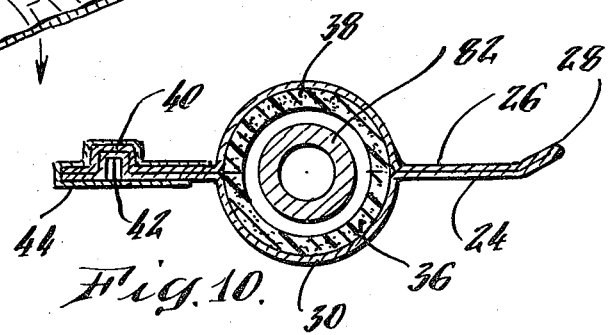

ASEPTIC CONNECTION BARRIER SYSTEM AND METHOD

BACKGROUND OF THE INVENTION

This invention relates to the administration of sterile medical solutions and, more particularly, to a system and method for assuring that connections for fluid conduits for such solutions are maintained in an aseptic condition.

Sterile medical solutions, such as for intravenous feeding, transfusions, peritoneal dialysis and the like, are frequently administered to patients through a fluid conduit a portion of which may be surgically implanted in the body. In such cases, generally, an in-dwelling conduit, such as a sterile cannula, has one end located within the body while a second end remains outside the body for connection to fluid administration conduit tubing. The medical solutions or fluids are commercially available packaged in containers such as flexible plastic bags or glass bottles. Separate sterile, plastic, disposable administration tubing is used to pass the contents from such bags through the in-dwelling conduit into the patient's body. The bag, administration tubing and in-dwelling conduit must form a sterile fluid circuit. Therefore, it is essential that any connection between them be established and maintained in an aseptic condition to avoid contamination.

In continuous ambulatory peritoneal dialysis multiple daily exchanges of the sterile fluid are performed by the patient through a flexible in-dwelling cannula which is surgically implanted into the peritoneal cavity and sutured in place so that one end of the cannula is located within the cavity and the second end, or junction site end, remains outside the body cavity to form a convenient, reuseable, sterile fluid conduit to the patient's peritoneal cavity. The administration tubing set is connected to the dialysis fluid containing-flexible bag by a plastic attachment at one end, presently known as a "spike," and to the in-dwelling flexible cannula with a special, comparatively permanent, sterile attachment at the second end, known as the "junction site." The procedure of penetrating the bag with the spike is known as "spiking in." For each fluid administration, the patient "spikes in" to the fluid inlet port of a new bag and allows the fluid to flow by gravity into the peritoneal cavity. The bag is generally wrapped around the fluid inlet port-spike connection and remains in place on the body during ambulation, during which time the bag, administration tubing set and in-dwelling cannula remain attached to one another. After the prescribed fluid dwell time, the bag is placed below the patient's peritoneal cavity and fluid from the cavity is allowed to drain by gravity into the bag which is then replaced with a new bag and the process of fluid administration repeated.

Continuous ambulatory peritoneal dialysis requires that administration, dwell and emptying be performed at regular and frequent intervals, such as four times a day, by the patient. In order to prevent infection and to minimize touch contamination of the spike connection site during and between bag changes, prior art systems rely on wrapping the connection site with an antiseptic containing absorbent material, such as a povidone iodine impregnated gauze sponge, surrounding the gauze by subsequent layers of unsaturated gauze and taping the wrapping in place. For each administration, the wrapping is removed and replaced.

Present commercial attempts at minimizing environmental and touch contamination require the patient remove povidone iodine antiseptic sponges from a container, separately remove sterile gauze sponges from another container or envelope, apply the swab dressing to the spike connection site and place the gauze sponge around the dressing after which the patient must peel the backing off tape and separately apply it around the dressing and gauze sponges to hold them in place around the connection. Thus, not only must the patient make the tubing connection, that is "spiking in," but he must then immediately manually carry out the several described steps to establish and maintain an antiseptic connection at the "spiking in" site while it remains exposed to the atmosphere. Although the components for doing this are provided as a kit, they nevertheless require considerable handling resulting in technical difficulties which arise from attempting to hold the connection site away from any possible sources of contamination while simultaneously attempting to unpack the dressing and gauze and tape strips. Thus, the chance of mishandling increased. Moreover, the risk of touch contamination are considerably increased. In addition, the gauze sponges remain exposed to the air which can cause the antiseptic to dry out leaving it ineffective. Accordingly, not only are such prior art approaches inconvenient, but they also leave much to be desired from the standpoint of patient safety.

SUMMARY OF THE INVENTION

The disadvantages associated with the prior art attempts at providing an aseptic protective barrier around sterile medical solution administration conduit connections are overcome through the provision of an aseptic connection barrier system and method which reduces patient inconvenience, mess and chance of leakage and minimizes the risk of touch contamination during application while ensuring continuous antiseptic activity, free from the chance of evaporation, around the entire connection site.

The foregoing is achieved, according to this invention, through the provision of an easy to apply, firm, plastic protection enclosure barrier device for surrounding the connection site and providing it with an aseptic barrier. The barrier device is comprised of a contoured plastic housing formed by mating cavity halves joined along a hinge line, an absorbent member contained within the interior of the housing and a sealing tab attached to one of the housing halves for holding them together when folded along the hinge line. In use, the absorbent member has antiseptic solution applied to it and the housing is positioned to surround the connection site and sealed in place to form a surrounding protective area barrier and seal.

An object of this invention is the provision of a system and method for providing a convenient, easy to apply barrier for assuring aseptic conditions around fluid conduit connections through which sterile medical solutions pass for administration to patients.

The plastic protection enclosure barrier device is advantageously removably held on an applicator support, such as a card in the open position to facilitate wetting of the inner absorbent member and provide a convenient and easy means for handling to facilitate application to the connection site while minimizing the risk of touch contamination and mishandling.

A further object of this invention is the provision of a aseptic connection barrier application system and method for facilitating convenient and safe application of the protective barrier about sterile medical solution fluid conduit connections.

Other objects, features and advantages of this invention will be further apparent from the following description of preferred embodiments thereof, taken in conjunction with the accompanying drawings, and the claims.

BRIEF DESCRIPTION OF THE DRAWINGS

FIG. 1 is a top perspective view of the aseptic connection barrier system, according to an embodiment of this invention, showing the system packaged in a sterile envelope;

FIG. 2 is a schematic illustration of a patient undergoing continuous ambulatory peritoneal dialysis showing the medical solution bag wrapped in a secure place on the patient with a "spike in" connection having been made;

FIG. 3 is a top perspective view of the aseptic connection barrier system shown in FIG. 2 but with the sterile envelope opened and the protection enclosure barrier device in position for application to a conduit connection;

FIG. 4 is a side view, in section, taken along the line 4—4 of FIG. 3 showing one of the protection enclosure barrier device matching housing cavities;

FIG. 5 is a view, in section, taken along the line 5—5 of FIG. 3 through the width of the aseptic connection barrier system and showing the matching housing cavities of the protection enclosure barrier device in the open position;

FIGS. 6, 7, 8 and 9 are perspective schematic views illustrating the method of applying the aseptic connection barrier device, according to an embodiment of this invention, to a spike site connection with a sterile solution plastic bag;

FIG. 10 is a view, in section, taken along the line 10—10 of FIG. 9, through the closed barrier device showing, in detail, the contamination impervious protective seal formed around the spike connection site.

DESCRIPTION OF THE PREFERRED EMBODIMENTS

An aseptic connection barrier system is shown in FIG. 1 in its sterile package form in which its kept until used by a patient. The sterile package 10 can be formed, as is known in the art, as a blister package in which a rigid support 12 such as a cardboard frame, is covered with sealable transparent plastic sheets 14 which enclose the aseptic connection barrier system 18 between them in sterile condition. For use, the package 10 is opened by peeling back one of the sheets 14 as illustrated at 16. The embodiment of an aseptic connection barrier system 18 illustrated in FIG. 1 is of a type which finds particularly advantageous use in continuous ambulatory peritoneal dialysis in which a patient carries a dialysis solution in a flexible plastic bag container together with an administration tubing set on the body, beneath the clothing, as illustrated in FIG. 2.

The aseptic connection barrier system 18 is best seen in FIG. 3 which shows the system 18 removed from the package 10 and in condition for application by the patient to the connection site of the sterile medical fluids conduit connection as described in greater detail hereinafter in reference to FIGS. 6 through 9. Referring to FIG. 3, there is shown a protection enclosure barrier device 20 formed from a self-supporting, sheet-like body member 22, preferably formed of plastic material, divided into two halves, 24 and 26, by a flexible hinge 28. Each half has a cavity, referred to at 28 and 30, respectively, formed therein. The cavities 30 and 32 are located in their respective halves, 24 and 26, of the member 22 so that, upon folding of the member 22 along the hinge 28, the cavities 30 and 32 will align with one another to form an enclosure or housing (see FIG. 10) surrounding the conduit connection site as explained below. Positioned within each cavity, 30 and 32, are compressible, absorbent semicylindrical liner members, 36 and 38, respectively, which are capable of retaining antiseptic liquid.

The plastic member 22 has formed therein, in addition to the cavities 30 and 32, a means for providing a fluid seal at a location opposite that of the hinge 28 when the member halves are folded to align the cavities and abut one another. Thus, the member halve 26 has an L-shaped channel or grove 40 formed therein while the member halve 24 has a correspondingly shaped ridge or projection 42 which will mate with the channel 40 when the halves are folded into abutting relationship and form a tight seal (FIG. 10). A tape closure 44 is attached to the member half 26 and may conveniently comprise a pressure sensitive tape with a release liner, as is known in the art, to secure the halves together at a conduit connection site in a tight fitting, sealed relationship.

The protection enclosure barrier device 20 is removably mounted in a rigid support 46, which may be made of cardboard, in a manner such that the projections resulting from the formations of the cavities 30 and 32 fit snugly into the openings 48 and 50, respectively, in the support and are held in place by the tabs 49 and 51, respectively (FIG. 8). As seen in FIG. 4, the device 22 is mounted at slight angle to the surface of the support to facilitate its alignment with the spike connection as explained below.

The support 46 also carries a source of antiseptic liquid in the form of a applicator tube 52 removably attached, by tab holder 53, thereto which may contain an antiseptic such as povidone iodine which applied by the patient-user to the compressible absorbent liner member, 36 and 38, prior to surrounding the conduit connection site. By "absorbent" material is meant any substance which is capable of retaining antiseptic liquid for use and not reacting therewith irrespective of whether the substance is one which relies on hydration of hydrophilic fibers, such as cellulosic fibers, or entrappment in cells of a hydrophobic material. One such substance of the latter type may advantageously comprise polyurethane ester foam. The support 46 also contains means to facilitate alignment, such as indicia, illustrated at 54, or small alignment "bumps" or posts, to illustrate the manner in which the device 20 is to be aligned with a conduit connection site to form an aseptic barrier therearound and thus facilitate its correct use. In addition, the support 46 may contain other information helpful to the patient.

As shown in FIGS. 1 and 3, the support 46 contains a cover portion 56, which may be hinged in relation to the remainder of the support by the use of score lines 58, to provide additional protection over that portion of the support containing the tube 52 as well as to provide protection of the entire system 18 by providing a height barrier, through the edge 60, so that the system 18 is not crushed or damaged when other systems are stacked thereon for packaging and shipping. At the same time, by providing only a half cover 56, as shown, the contents are visible to the user when in the sterile package 10.

The cavities 30 and 32 are contoured and configured to approximate the configuration of the conduit connection to be surrounded in order that close engagement is achieved. In this manner, the compressible absorbent liner members 36 and 38 form a contiguous cylindrical barrier in contact with the conduit connection so that both the absorbent liner and antiseptic fluid thereon surrounds the connection to ensure aseptic conditions. That is, there results a virtual antiseptic seal about the connection. Also, through a relatively tight fitting engagement a fluid seal may be achieved where the conduit itself passes through the housing formed around it by the barrier device. The above will be better understood by referring to FIGS. 6, 7, 8 and 9 illustrating the use of the barrier device 20 in association with the type of conduit connection used in peritoneal dialysis, previously described, in which the administration tubing which is connected to the in-dwelling cannula inserted in the body is connected at its other end to the dialysis fluid container through an attachment known as a spike.

Referring first to FIG. 6, there is shown a dialysis solution plastic bag container 70 having an injection port 72 and a fluid inlet port 74. In order to form a sterile fluid circuit from the container 70 through the administration tubing 76 the patient must "spike in" by penetrating the container fluid inlet port 72 with the spike, referred to generally at 78.

The spike 78 contains a heavier handle portion 80 by which it may be grasped as well as the "spike" portion 82 which matingly engages the port connector 74 as inserted therein to penetrate the bag container 70. The spike illustrated is of the type used in connection with the continuous ambulatory peritoneal dialysis system available from Travenol Laboratories, Inc. The handle 80 of the spike 78 includes a continuous peripheral shoulder 84. The cavities 30 and 32 are therefore contoured and configured to to approximate the connection made between the port connector 74 and the spike 78 and provide a tight seal and an aseptic barrier therearound. Accordingly, as seen also in FIGS. 3 and 6, the cavities 30 and 32 each contain respective channels or groves 86 which engage the spike shoulder 84 when the halves are closed around the connection site. In addition, the cavities 30 and 32 are configured of stepped cylindrical shapes the outermost of which, illustrated at 88 and 90, may be sized to tightly engage the port connector 74 to form a tight seal while the inner, larger cylindrical portions, 92 and 94, are configured to hold the absorbent liners 36 and 38 so that they are compressed by the connection made. The intermediate cylindrical cavity portions 96 and 98 provide an additional channel reservoir to accomodate incidental leakage and minimize fluid migration from the interior of the housing to the exterior.

The method of forming and maintaining an antiseptic environment at the connection site when "spiking in" is illustrated in FIGS. 6, 7, 8 and 9. After peeling the protective film 16 to expose the aseptic connection barrier system 18, the patient folds back the cover 56, removes the tube 52 and applies antiseptic to the compressible absorbent liners 36 and 38. The patient then grasps the support 46 with one hand and aligns the connection which has been made in "spiking in" with the indicia 54, the support card 46 and positions the connection over the barrier device member half 24, as shown in FIG. 6. The patient then grasps the closure tape 44, as shown, which is attached to the barrier device member half 26 to remove that half from its opening 50 in the support card 46 and fold the member along the hinge 28 to align the two cavities and bring the halves into abutting relationship, as shown in FIG. 7. The patient then presses the halves together with the fingers, as shown, to apply pressure to cause the projection 42 to enter groove 40 and form a seal. The patient then removes the member half 24 from its opening 48, as shown in FIG. 8, removes the release liner from the pressure sensitive closure tape 44 and secures the two halves together, as shown in FIG. 9. At this time, the compression of the liners 36 and 38 will have caused the antiseptic liquid thereon to distribute itself around the connection site providing an antiseptic environment. In addition, according to one embodiment of the invention, the body member 22 may be fabricated from plastic material in a manner such that it is sufficiently flexible to permit further assurance of distribution of the liquid through squeezing of the barrier device by the fingers, as shown in FIGS. 8 and 9.

As FIGS. 6, 7, 8 and 9 illustrate, the support 46 contains a sufficient area which can be firmly grasped by the patient and the entire procedure for creating and maintaining the aseptic barrier environment is carried out with a maximum convenience of handling and a minimum of risk of mishandling. That is, the steps involved are reduced and simplified and the risk of contamination through touching is virtually eliminated.

It will be understood that although the embodiment shown is that which finds particularly advantageous use in connection with the commercially available "spiking in" system for continuous ambulatory peritoneal dialysis finding widespread use today, the invention is applicable to other situations in which an aseptic environment must be maintained about a sterile medical solution conduit connection. Thus, the invention finds utility and applicability to other procedures and systems for administering sterile medical fluids, such as intravenous feeding. It will be understood, of course, that the configuration of the cavities can be varied to suit the connection site involved. Or, a "universal" type enclosure of configuration capable of enclosing several different types of connections and relying on the compressibility of the absorbent members together with appropriate mating channels and projections to provide the necessary fluid seal.

In the embodiment illustrated, the configuration of the spike, particularly the shoulder portion, and the complimentary configuration of the cavity facilitated alignment of the parts and also assured that the spike was "locked in" in a snug fit and that a good fluid seal was established. Tolerances of dimensions should therefore be selected to ensure proper sealing retention of liquid and controlled compression. The absorbent material will then be kept moist, an important advantage because some antiseptic liquids such as povidone iodine are more active when wet since they flow and protect better.

In the embodiment shown, the absorbent cylindrical members were made of a polyurethane ester foam of 30–80 pores per square inch, one inch long, 0.625 inches outside diameter and 0.125–0.160 wall thickness. It will be understood that in certain applications the antiseptic fluid may be retained in the cavities by means other than "absorbent" members such as a stable, highly viscous fluid gel or enclosed by a breakable membrane. The barrier device can be of rigid plastic or somewhat flexible plastic, provided only that the device is firm in the sense of being self-supporting and may be produced by a variety of thermal plastic forming methods including vacuum forming and injection molding techniques. The embodiment illustrated was fabricated from 0.015 inch polyvinyl chloride by vacuum forming.

Although the closure tape illustrated is a clear polyester, pressure sensitive tape with a release liner, it should be understood that alternate closures such as paper tapes, interferance lids, undercuts and mechanical snaps may be used. For example, the projection and groove illustrated in the embodiment shown for a good seal can be configured to provide a tight closing fit for maintaining the halves in abutting relationship also.

The entire aseptic connection barrier system which includes the barrier device mounted on the applicator support provides several advantages. These include holding the barrier device in the open position to facilitate wetting of the inner absorbent members, enabling easy and convenient handling of the device without risk of contamination, facilitating alignment of the device and providing instructions and directions for use in a unit without the need for separate papers which can be lost. The barrier device itself provides a easy to apply rigid seal around the "spike in" area, insures antiseptic activity since evaporation of the antiseptic containing solution is minimized, as is the chance of leakage, and virtually eliminates the risk of touch contamination and patient mess during application.

We claim:

1. An aseptic connection barrier device for surrounding a connection site formed in conduit used for administering sterile medical fluids comprising a self-supporting, sheet-like body member divided into two halves by a flexible hinge formed therein, the two halves being capable of abutting one another when the member is folded about its hinge, each of the halves having a contoured cavity formed therein such that the cavities align with one another to form a housing capable of surrounding the conduit connection site when the member halves are folded into abutting relationship, the cavities in the member being each contoured to matingly approximate the configuration of the conduit connection so that the housing formed by alignment of the cavities provides a close fitting aligning and mating engagement with the conduit connection site, compressible absorbent means located in each of the cavities for holding an antiseptic medium, the absorbent means being positioned such that, when the cavities are aligned to form the housing surrounding the connection site, the conduit connection contacts and compresses the absorbent means, means including recesses formed in the member to receive portions of the conduit connection for providing a fluid seal on the body member exteriorly of the housing when surrounding the connection site and further comprising reservoir channels formed in the member to accommodate leakage and a ridge formed in one half of the member and a channel formed in the other half of the member to receive the ridge in mating engagement when the halves abut one another, the ridge and channel being formed on that portion of the member apart from the hinge and means for securely maintaining the member halves in abutting relationship.

2. An aseptic connection barrier system for conveniently providing an aseptic environment around a connection site in a conduit administering sterile fluids comprising a rigid, essentially planar sheet-like support, the support having an opening into which is removably fitted a self-supporting, sheet-like body member divided into two halves by a flexible hinge formed therein, the two halves being capable of abutting one another when the member is folded about its hinge, each of the member halves having a cavity formed therein, the two halves being capable of abutting one another when the member is folded about its hinge, each of the member halves having a cavity formed therein, the cavities aligning, when the member is folded about its hinge, to form a housing capable of surrounding the conduit connection site, means within at least one of the cavities for holding an antiseptic fluid for application to the connection site when the housing surrounds it, the housing approximating the configuration of the connection site so as to provide alignment and close fitting engagement with the connection site when the housing surrounds it, the member being positioned on the support in an open, substantially flat position with the halves having the cavities projecting into the opening in the support to facilitate positioning of one half of the member adjacent to the connection site, with the location of the opening in the support being selected so as to provide a support portion which can be conveniently manually held while the member other half is folded over the one half to surround the connection site, and means for securely maintaining the member halves in folded, abutting relationship.

3. An aseptic connection barrier system as claimed in claim 2 further comprising a source of an antiseptic medium removably attached to the support.

4. An aseptic connection barrier system as claimed in claim 3 wherein the support opening for holding the body member is located adjacent one edge of the support and sufficient space remains on the support to form said support portion for gripping the support securely between a thumb and forefinger for holding while aligning the body member with a connection site.

5. An aseptic connection barrier system as claimed in claim 4 further comprising means on the support for facilitating alignment of the body member with the connection site.

* * * * *